United States Patent
Salari (10) Patent No.: US 11,752,269 B2
(45) Date of Patent: Sep. 12, 2023

(54) SPRING LOADED MEDICAL NEEDLE-FREE INJECTION SYSTEM

(71) Applicant: INTEGRIMEDICAL LLC, Phoenix, AZ (US)

(72) Inventor: Hassan Salari, Irvine, CA (US)

(73) Assignee: INTEGRIMEDICAL LLC, Phoenix, AZ (US)

( * ) Notice: Subject to any disclaimer, the term of this patent is extended or adjusted under 35 U.S.C. 154(b) by 0 days.

(21) Appl. No.: 17/123,968

(22) Filed: Dec. 16, 2020

(65) Prior Publication Data

US 2021/0187198 A1    Jun. 24, 2021

Related U.S. Application Data

(60) Provisional application No. 62/949,984, filed on Dec. 18, 2019.

(51) Int. Cl.
*A61M 5/30* (2006.01)
*A61M 5/315* (2006.01)
*A61M 5/20* (2006.01)

(52) U.S. Cl.
CPC ............ *A61M 5/30* (2013.01); *A61M 5/2033* (2013.01); *A61M 5/3158* (2013.01); *A61M 5/31571* (2013.01)

(58) Field of Classification Search
CPC .... A61M 5/30; A61M 5/3007; A61M 5/3015; A61M 5/2033
See application file for complete search history.

(56) References Cited

U.S. PATENT DOCUMENTS 2,550,053 A * 4/1951 Ferguson ................ A61M 5/30
604/68
4,874,367 A * 10/1989 Edwards ................ A61M 5/30
604/72

(Continued)

FOREIGN PATENT DOCUMENTS

AR        120781 A1    3/2022
CN      205108596 U *  3/2016

(Continued)

OTHER PUBLICATIONS

Comfort-in Needle Free Injection System, "How to Use the Comfort-in (TM) Needle-Free Injector | Needle Free Injection", May 2018, youtube.com <<https://www.youtube.com/watch?v=pJ8LmGNWg2c>> (Year: 2018).*

(Continued)

*Primary Examiner* — William R Carpenter
(74) *Attorney, Agent, or Firm* — Kutak Rock LLP (57) ABSTRACT

Disclosed is a fluid injection device for a needle free syringe is provided that is spring-loadable and comprises a trigger positioned within the housing and actuated by depression of a push-button disposed opposite the dispensing end at an external actuation surface disposed transverse to the injection axis. The trigger has a trigger latch configured to release a trigger catch as heaving part of the spring-loaded piston of the device. The trigger catch is configured to urge the trigger latch in a direction transverse to the injection axis when the piston moves from the unloaded position to the loaded position. The compression spring is retained around the piston and retained within the housing by a piston head. The device further comprises a syringe adapter and a safety cap which prevents accidental triggering.

23 Claims, 7 Drawing Sheets

(56) References Cited

U.S. PATENT DOCUMENTS

| | | | | |
|---|---|---|---|---|
| 5,024,656 | A | * | 6/1991 | Gasaway .............. A61M 5/30 604/141 |
| 5,569,189 | A | * | 10/1996 | Parsons ............ A61M 5/1782 604/22 |
| 5,599,302 | A | * | 2/1997 | Lilley ................. A61M 5/30 604/135 |
| 5,599,602 | A | * | 2/1997 | Leonard ............... B29C 48/35 428/56 |
| 6,004,286 | A | * | 12/1999 | Bellhouse .......... A61M 5/3015 604/140 |
| 8,529,499 | B2 | * | 9/2013 | Matusch .......... A61M 5/31501 604/68 |
| 8,734,384 | B2 | | 5/2014 | Brooks |
| 9,421,335 | B2 | | 8/2016 | Sanofi-Aventis |
| 2005/0000711 | A1 | * | 1/2005 | Hurlstone ............. A61M 5/30 173/19 |
| 2006/0089593 | A1 | | 4/2006 | Landau et al. |
| 2007/0118094 | A1 | * | 5/2007 | Bingham ........... A61M 5/3158 604/500 |
| 2009/0137948 | A1 | * | 5/2009 | Marshall ............... A61M 5/30 604/68 |
| 2010/0036326 | A1 | * | 2/2010 | Matusch ............... A61M 5/30 604/198 |
| 2011/0218500 | A1 | * | 9/2011 | Grunhut ............. A61M 5/2033 604/228 |
| 2016/0022910 | A1 | * | 1/2016 | Tsui ................... A61M 5/3015 604/500 |

FOREIGN PATENT DOCUMENTS

| | | |
|---|---|---|
| CN | 205322929 U | 6/2016 |
| EP | 4076593 | 10/2022 |
| KR | 101000589 B1 | 12/2010 |
| TW | 202135877 A | 10/2021 |
| WO | 2006118616 A1 | 11/2006 |
| WO | 2012154025 A2 | 11/2012 |
| WO | 2013019939 A2 | 2/2013 |
| WO | 2021127249 A1 | 6/2021 |

OTHER PUBLICATIONS

Comfort-In Needle Free Injection System, "How to Charge the Comfort-In (TM)", Mar. 2017, Youtube.com <<https://www.youtube.com/shorts/RrRKeluNDOM>> (Year: 2017).*

"International Search Report and Written Opinion for International Application No. PCT/US2020/065716, Search completed on Apr. 14, 2021, dated Apr. 19, 2021."

"Office Action Received for Bangladesh Patent Application No. 376/2020, dated Dec. 15, 2021."

"Adverse Report Received for Malaysia Patent Application No. PI2022003287, dated Oct. 17, 2022."

"Notice of Allowance Received for Bangladesh Patent Application No. 376/2020, dated Sep. 18, 2022."

* cited by examiner

SPRING LOADED MEDICAL NEEDLE-FREE INJECTION SYSTEM

CROSS-REFERENCE TO RELATED APPLICATIONS

This application claims priority pursuant to 35 U.S.C. 119(e) to U.S. Provisional Patent Application Ser. No. 62/949,984, filed Dec. 18, 2019, the entire disclosure of which is incorporated herein by reference.

FIELD OF THE INVENTION

The present invention relates to a medical injection device and kit. More particularly, the present invention relates to an improved spring loaded needle-free hypodermic injection device.

BACKGROUND OF THE INVENTION

Medical needle-free injection technologies do not pierce the skin of a subject with a conventional needle to deliver medication to a subject. Some benefits of needle-free injection compared to conventional injections may include: reduced risk of needle stick accidents; eliminated risk of disease transmission from re-used needles; reduced bleeding or bruising; faster and more reproducible drug delivery; not subject to needle-phobia; and better suited to self-administration. Depending on its specifications, a needle-free injection device may be suitable for subcutaneous, transdermal or intramuscular use.

Injection free devices inject liquid or powdered medicine through micro orifices by rapidly applied high pressure. Coil springs, gas-springs and explosives supply the rapid high pressure. Inventors are constantly improving on such devices making them safer to use by healthcare professionals and patients.

For instance, Thai et al. in PCT patent application WO2012154025 A2 discloses a spring-powered needle-free hypodermic injector. The spring is associated with a piston head, which are both slidably housed within the handle of the injector. When compressed, the spring is positioned in the handle opposite the open end of the device and the open end is connected to the plunger end of a needle-free syringe that holds the fluid to be injected. The compressed spring is held in place by the stopper of a trigger which is pivotally mounted to the handle near the opening of the device. When trigger-actuated by displacing the trigger stopper from piston head, the power stored in the spring drives the piston head to depress the plunger of the syringe and force the fluid from the nozzle into the subject's skin.

A return spring returns the trigger to the non-actuated position. A slid-able safety lock on the handle proximal the opening of the device can be slid under an end of the trigger to prevent accidentally actuating the device. The injector, however, may not b e used by users other than professionals in clinical setting.

Nzike et al. in U.S. Pat. No. 9,421,335 B2 proposed a clutch mechanism for rotationally locking and releasing the dose member within a drive sleeve. The clutch, however, lacks positive safety against accidental triggering.

Most of the marketed needle-free injectors have serious limitations. For example, the placement of a trigger on the side of the injector may not be convenient for self-injection, as it may be difficult for the user to orient the injector perpendicular to the user's skin and hold it securely there with the user's thumb pointing towards the user's body. When an injector is not held securely and perpendicularly against the skin, it may fail or cause medication leakage during injection. In addition, the spring force of some injectors is only sufficient to inject a small volume of fluid. Small volume injections are not optimal for some users/patients. In some injectors, the form factor is fixed, with the result that the injector cannot be modified to increase its spring force for higher volume injections. As an alternative to using spring power, certain needle-free injectors use compressed gas, battery power or a pyrotechnic charge to drive fluid through the nozzle and into or through the skin or tissue of the subject.

For example, Boyd et al. in U.S. Pat. No. 8,734,384 B2 discloses a compressed gas injector which operates by pushing the piston into a fluid filled chamber, which pressurizes the fluid and creates a fluid jet as it empties through a jet orifice. Actuation of the injector in this device is preferably triggered from pressing the device against the patient's skin. Triggering the device however is not handy and the gas pressure pistons can be misused or mishandled and require resupply with limited shelf life.

Some needle-free injectors are intended for disposal after a single use, while others are reloadable. Certain other needle-free injectors inject powdered substances as micro projectiles.

Improvement on the state of art is obviously needed. More specifically, safer and handier mechanisms are in demand which can excerpt precision metered doses at precision selected pressures for self-administering safety. Hand power reloading is preferred over prepackaged consumable power cartridges.

The object of the invention is to improve on the state of the art by overcoming the listed and other shortcomings in needle-free liquid medicine delivery into human or animal bodies.

SUMMARY OF THE INVENTION

The above problems and others are at least partially solved and the above objects and others realized in a process, which, in some embodiments, according to the teachings of this invention, uses a medical fluid injection device, comprising: a housing having an inner surface and an outer surface which extend from a trigger end to a dispensing end along an injection axis, the trigger end comprising an external actuation surface disposed transverse to the injection axis; a syringe adapter removably or irremovably affixed to the dispensing end of the housing, the syringe adapter configured to retain a needle-free syringe such that a plunger of the needle-free syringe is movable within the housing along the injection axis; a piston retained within the housing by the syringe adapter and movable along the injection axis between a loaded position proximal to the trigger end and an unloaded position proximal the dispensing end, the piston comprising a piston head proximal to the dispensing end and a trigger catch proximal to the trigger end of the housing, the piston head being movably positioned to bias the plunger of the needle-free syringe along the injection axis; a compression spring retained around the piston by the piston head, the piston and compression spring sized relative to the housing such that the compression spring is compressible along the injection axis within the housing; and a trigger mounted within the housing proximal the trigger end and movable between a non-actuated position and an actuated position by depression of a push-button disposed at the external actuation surface of the housing, the trigger comprising a trigger latch configured to engage the trigger catch when the trigger is in the non-actuated position and the piston is in the loaded position, and to release the trigger catch when the trigger is in the actuated position, wherein the trigger catch is configured to urge the trigger latch in a direction transverse to the injection axis when the piston moves from the unloaded position to the loaded position.

The trigger catch of some embodiments of the fluid injection device comprises an annular engagement surface extending radially outward from the injection axis and facing towards the dispensing end of the housing. The trigger latch of some embodiments comprises an engagement surface extending inwardly towards the injection axis and facing towards the trigger end of the housing, and which engages the annular engagement surface of the trigger catch when the trigger is in the non-actuated position and clears the trigger catch when the trigger is in the actuated position. The trigger catch of the fluid injection device of some embodiments further comprises an annular beveled surface which faces away from the injection axis towards the trigger end of the housing. The trigger latch of some embodiments further comprises a beveled surface which faces towards the injection axis and towards the dispensing end of the housing.

The trigger of some embodiments further comprises a lever biased towards the push-button by a return spring disposed within the housing. The return spring in some embodiments is a clip spring biased against the lever of the trigger.

The fluid injection device of some embodiments further comprises a movable safety cap for blocking depression of the push-button. The safety cap of some such embodiments is pivotally mounted to the external actuation surface of the housing and popped up by the fingernail of the thumb of a self-injecting patient.

The interior surface of some embodiments of the housing of the fluid injection device comprises a portion extending towards the injection axis and which blocks the compression spring from contacting the trigger.

The syringe adapter of the fluid injection device of some embodiments comprises an outer surface that extends away from the injection axis beyond the outer surface of the housing. The syringe adapter of some embodiments is removable.

The housing of some embodiments is capable of being configured to removably accept alternatively configured syringe adaptors.

The piston and the compression spring of some embodiments is capable of being removable from the housing when the syringe adapter is removed from the housing. The housing of some embodiments is capable of being configured to removably accept one or both of alternatively sized pistons and springs.

Various embodiments of this disclosure relate to a kit comprising: a fluid injection device of the type defined above; and a loader configured to receive the fluid injection device on an interior retaining surface comprising a lip adapted to engage the outer surface of the syringe adapter of the fluid injection device, wherein the loader is movable about a hinge between an open state and a closed state to extend a plunger into an open end of the syringe adapter to contact the piston head so as to push the piston from the unloaded position into the loaded position.

In some embodiments, the syringe adapter of the fluid injection device is capable of being removable and the kit of some embodiments further comprises one or more additional compression springs, each of which is distinctly configured to provide a different spring force. In some embodiments, the syringe adapter contains features that allow the syringe adapter to work smoothly with springs designed for the appropriate size of the syringe adapter. In some embodiments, the syringe adapter of the fluid injection device is capable of being removable and the kit of some embodiments further comprises one or more additional syringe adapters, each of which is configured to retain a different needle-free syringe.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

DETAILED DESCRIPTION OF A PREFERRED EMBODIMENT

As required, a detailed embodiment of the present invention is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 2:
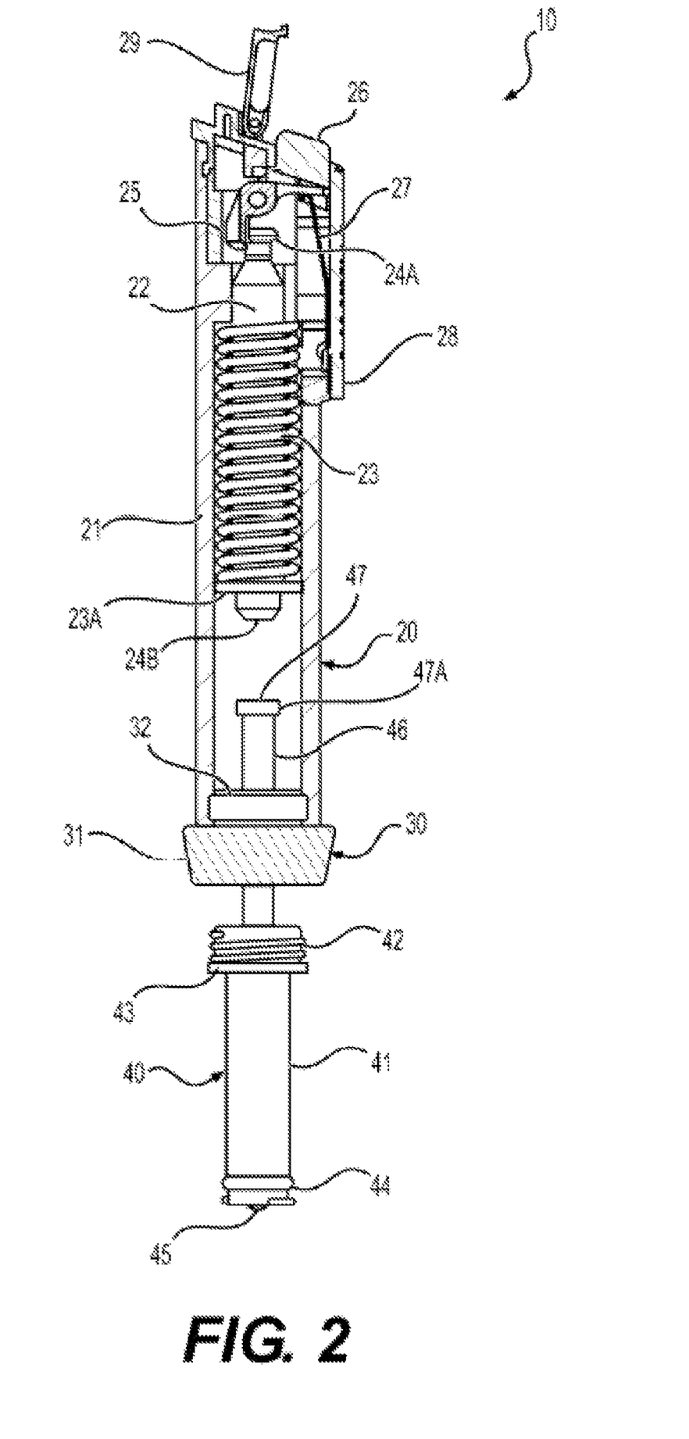
FIG. 2 shows an offset sectional view of the fluid injection device of FIG. 1, in a loaded and non-actuated state.
Figure 3A:
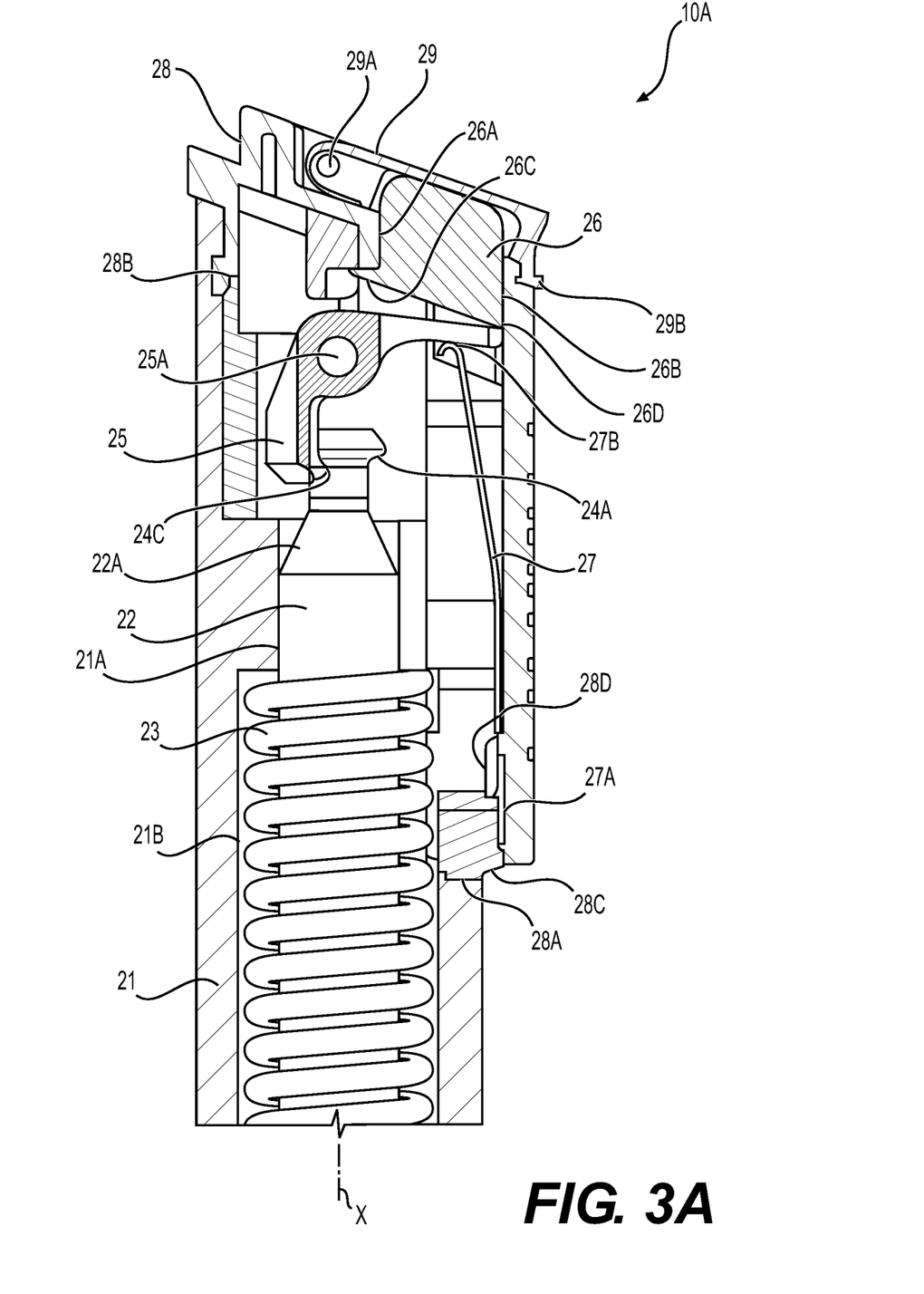
FIG. 3A shows a full sectional view of a portion of the fluid injection device of FIG. 1, in a loaded and non-actuated state.
Figure 3B:
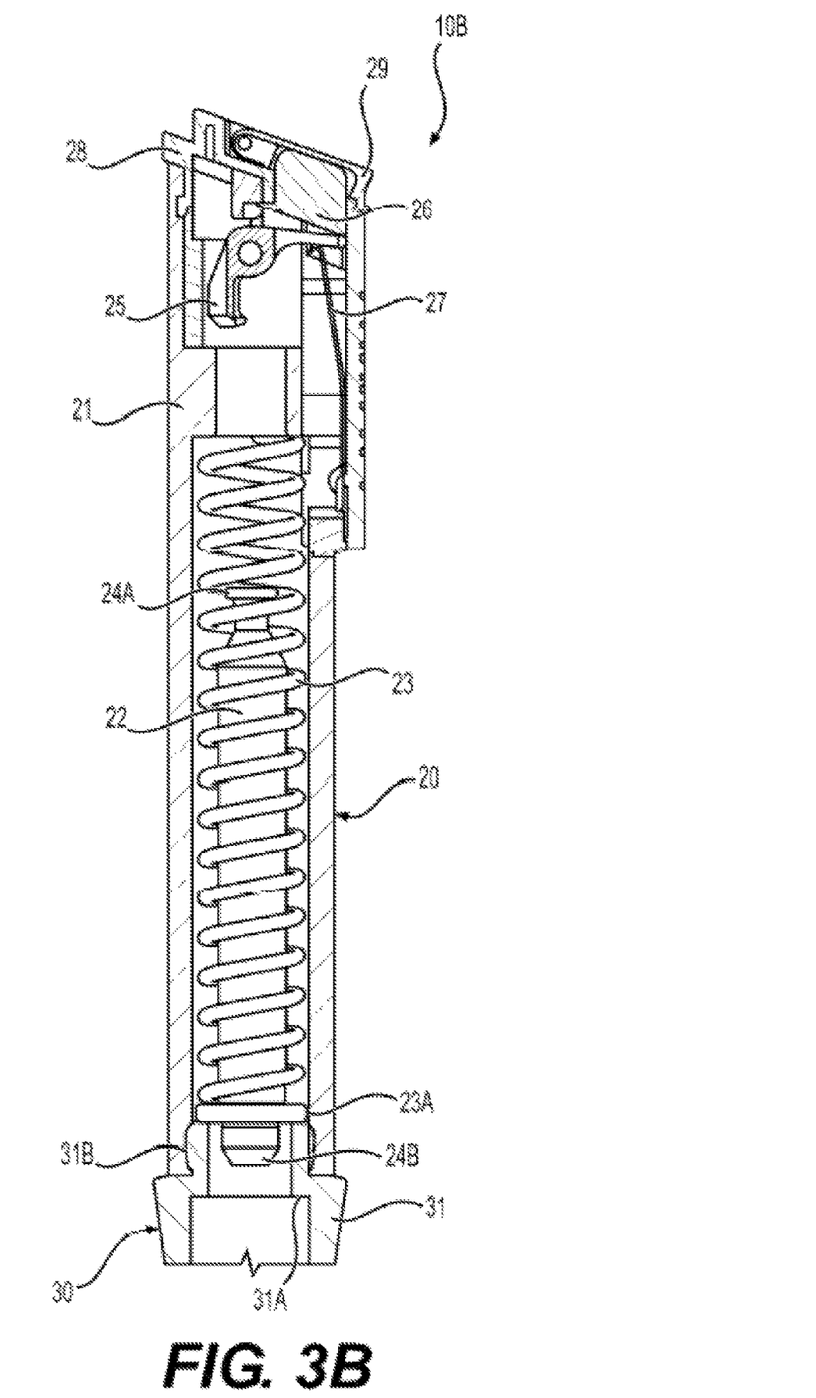
FIG. 3B shows a full sectional view of the fluid injection device of FIG. 1, in an unloaded and non-actuated state.
Figure 4A:
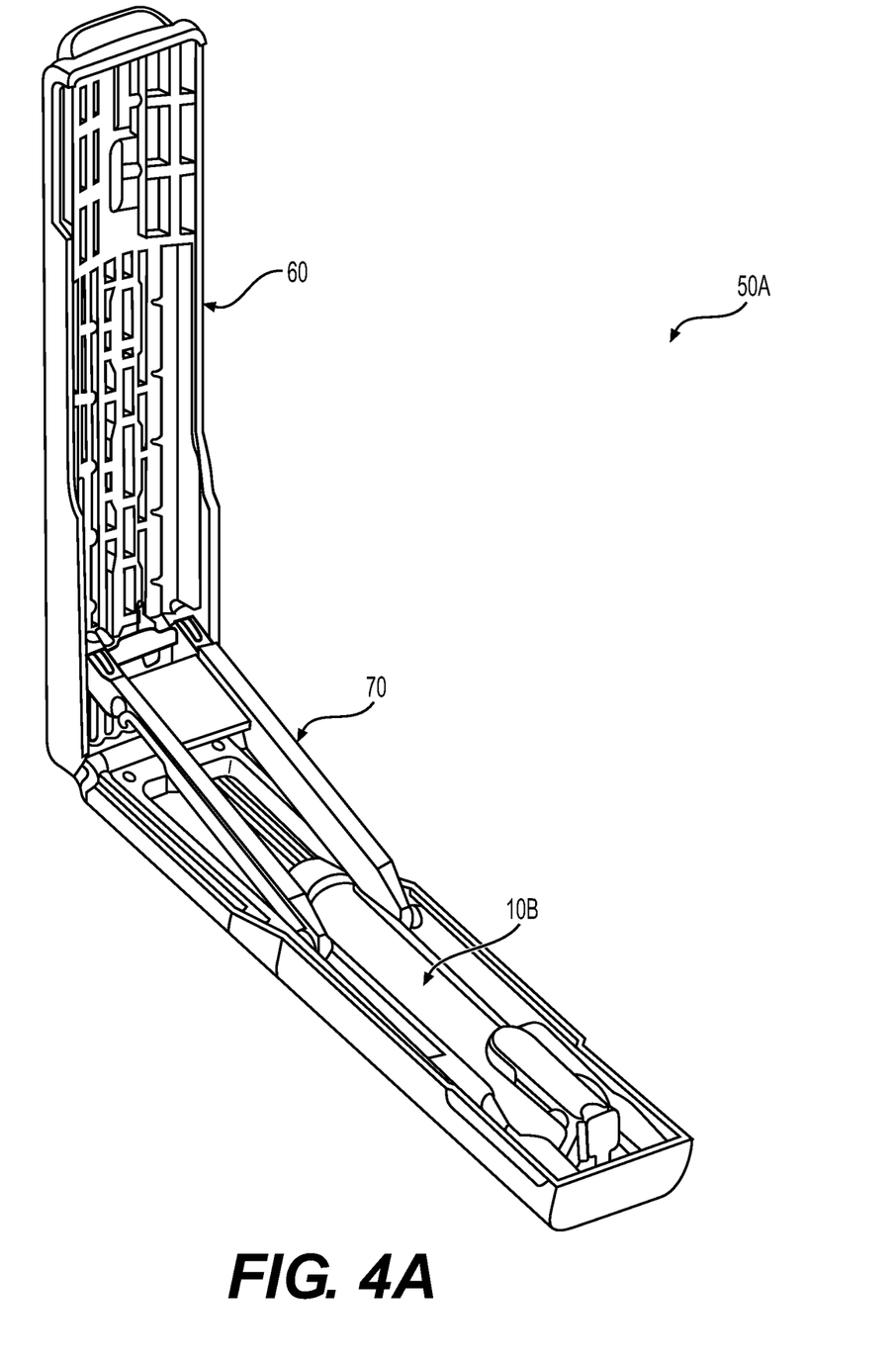
FIG. 4A shows an isometric view of an open loader retaining the fluid injection device of FIG. 1.
Figure 4B:
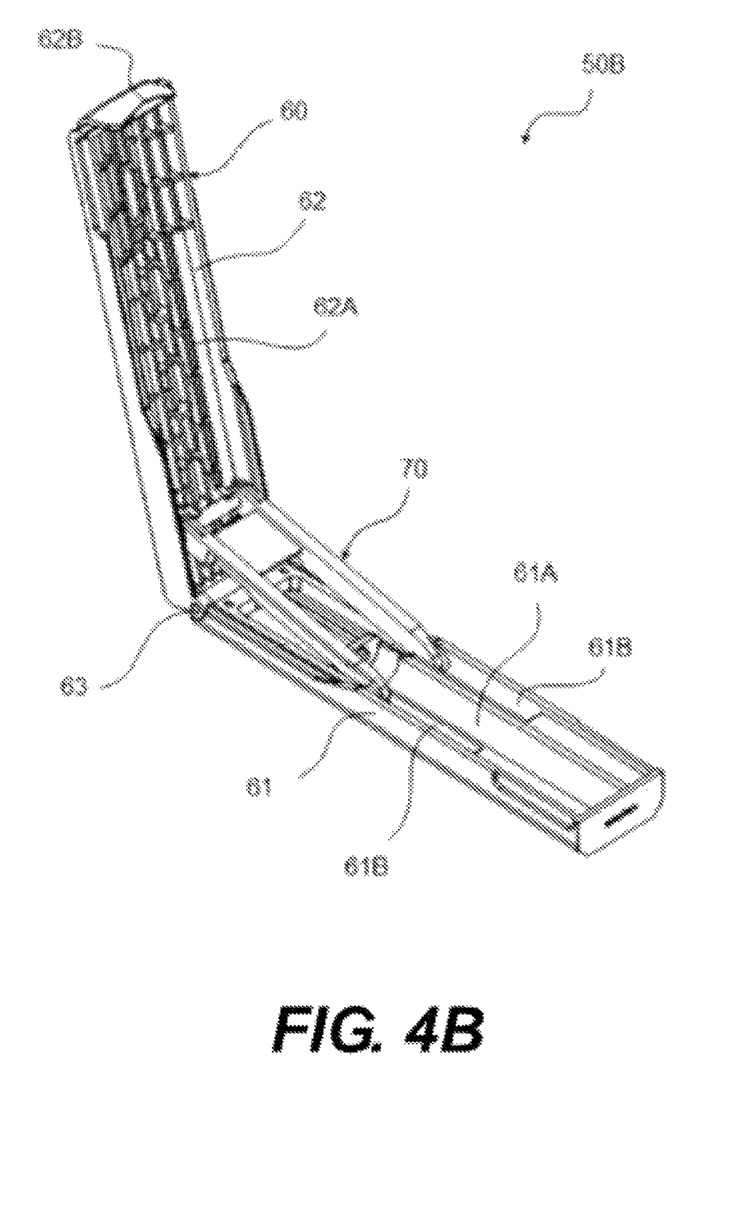
FIG. 4B shows a partially exploded view of the open loader of FIG. 4A without the fluid injection device assembled compact.
Figure 4C:
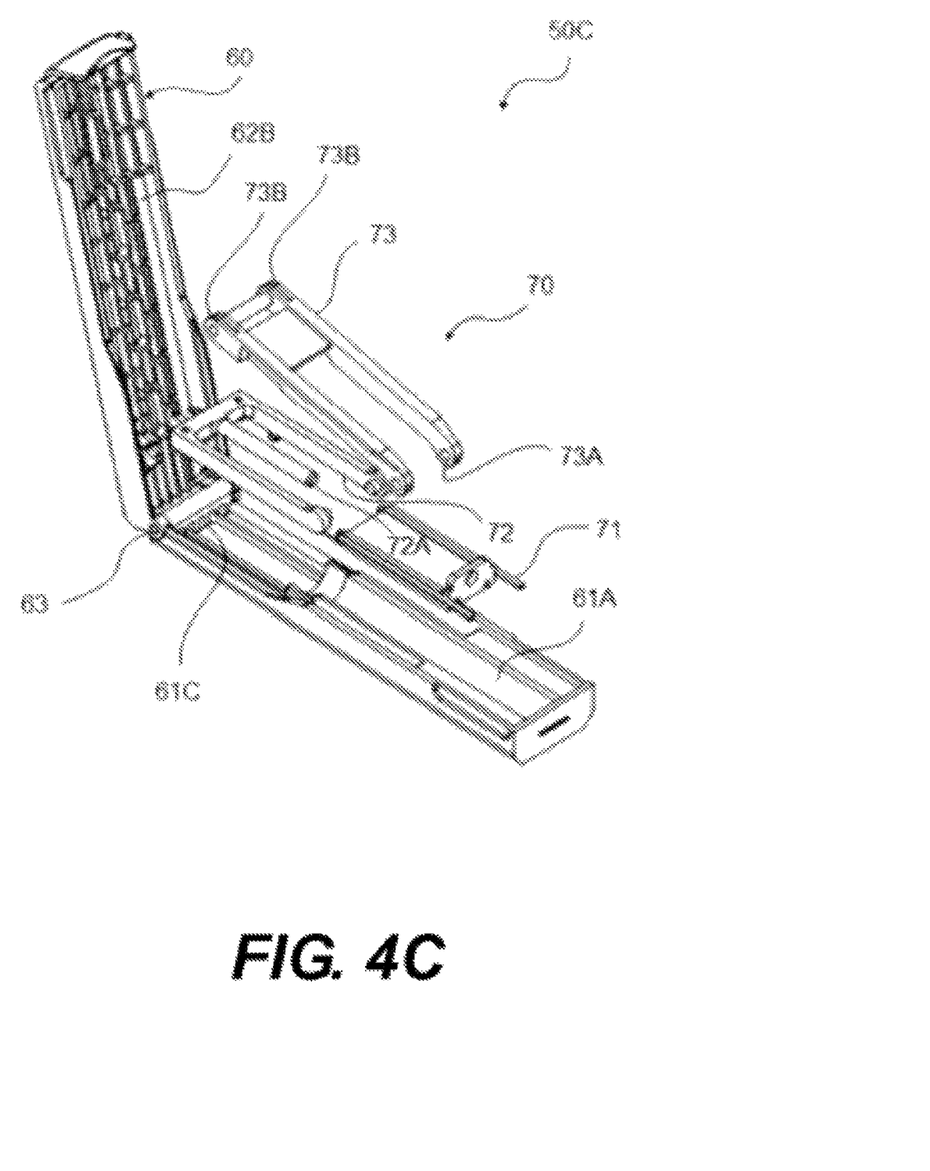
FIG. 4C shows a partially exploded view of the open loader of FIG. 4A without the fluid injection device disassembled and stripped apart.

The following description discloses the proposed fluid injector device for use with a needle-free syringe with preferred embodiment illustrated in FIGS. 1-3B along with its spring loader, which is shown in FIGS. 4A-4C.

Figure 1:
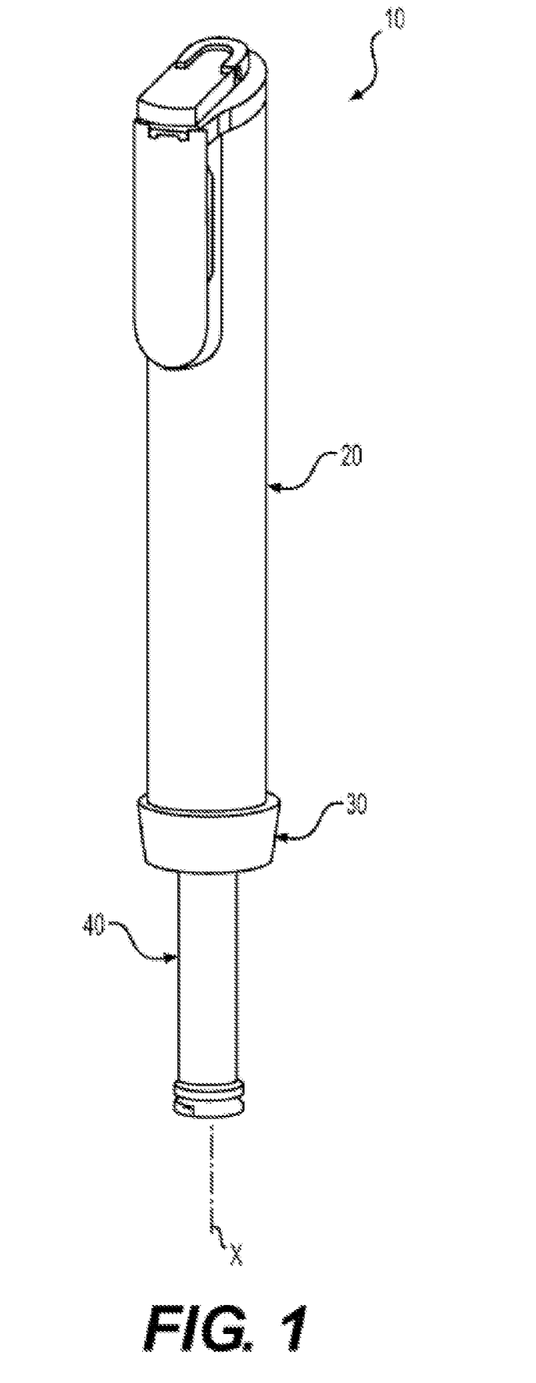
FIG. 1 shows an isometric view of a fluid injection device in accordance with an embodiment of the present invention, in a loaded state and attached to a needle-free syringe.

Attention is now turned to FIG. 1, which, in isometric view, illustrates injector 10, comprising of housing 20 with triggered spring loaded mechanism, needle-free syringe adapter 30 and needle-free syringe 40, whereas injector 10, housing 20, adapter 30 and syringe 40 are all aligned along dispensing axis X, which is the injection axis. Injector 10 is shown in its loaded state. However, after injection, injector 10 looks the same. Without reloading, triggering will not cause a secondary injection.

The housing and other components of the fluid injector device of various embodiments are made of stainless steel, for example, or any other suitable metal (e.g. zinc/chrome-plated carbon steel) or any other suitable rigid material, such as a rigid plastic (e.g. PC/ABS plastic) or the like. In some embodiments, the housing includes a generally continuous cylindrical metal (e.g. stainless steel, zinc, carbon, etc.) material tube inner and outer surfaces with openings only at the trigger end and the dispensing end. In some such embodiments, the only non-metal components enclosing the housing are located at the openings at the trigger end (e.g. the push button 26, clip spring 27, housing top retainer 28, and safety cap 29), and the dispensing end (e.g. the syringe). The wall thickness of the metal utilized for the housing is sufficient to support the internal components of the injector (e.g. spring, piston, etc.), and also to prevent significant sound created within the housing (e.g. from the spring/piston actuation) from escaping the sidewalls. This structure and the heavier and thicker metal material of the housing result in limiting the amount of sound that is produced by the injector during operation. The syringe itself functions to seal the dispensing end opening and absorb sound produced by the actuation mechanism (e.g. spring, etc.) during actuation. As such, the only point in which sound generated during actuation can travel outside of the housing is through the non-metal components at the trigger end (which in some embodiments is sealed by the non-metal components such as the push button, housing top retainer, safety cap, etc.). In addition to reducing the sound generated, the sound is directed away from the subject being injected, and is less likely to startle the subject during injection.

Embodiments of the housing include a variety of sizes depending on its intended manner of use. For example, the housing of some embodiments is sized and shaped to be held comfortably by the user in one hand (e.g. a cylinder of approximate dimensions 13 cm long×1.5 cm diameter). The user may be someone who is self-injecting, for example in the abdomen, arm, leg or another location of the body. Alternatively, the user may be a medical professional or technician who is injecting a human or animal subject.

Attention is now turned to FIG. 2, which, in isometric partial section view, illustrates injector 10 with housing 20 with mounted syringe adapter 30 in partial disassembly with syringe 40. Injector 10 is shown in its loaded state.

Housing 20 comprises body 21, piston 22 with trigger catch shoulder 24A and hammer tip 24B, piston stop 23A, loaded with coil spring 23, trigger catch 25, push button 26, clip spring 27, housing top retainer 28, and safety cap 29.

Adapter 30 comprises threaded socket 31 and threaded shoulder 32.

Syringe 40 comprises liquid medicine dispenser capsule 41, threaded head 42, head stop shoulder 43, dispensing tip 44 and injection nozzle 45 with one or more micro orifices.

The trigger end of the housing includes an external surface disposed transverse to the injection axis X. The trigger end of the housing further comprises a housing top retainer affixed to the external surface disposed transverse to the injection axis X of the housing. The housing top retainer further comprises an external surface disposed transverse to the injection axis X. The housing top retainer external surface disposed transverse to the injection axis X tapers downward towards the dispensing end of the syringe. This places the actuation surface in good position for the thumb of a user to actuate the device for self-injection by depression of a push-button disposed at the external actuation surface.

The dispensing end of the housing is connected to a syringe adapter configured to retain the needle-free syringe such that the plunger of the needle-free syringe is movable within the housing along the injection axis X. For example, in some embodiments, threading within the open end of the syringe adapter mates with the housing of the needle-free syringe. In certain embodiments, the threading consists of 3 threads. In other embodiments, the threading consists of 2, 3, 4, 5, 6, 7, 8 or more threads. The threading in some embodiments is configured to mate with commercially available syringes.

The syringe adapter is affixed to the dispensing end of the housing. In certain embodiments, the syringe adapter is removably affixed. For example, the syringe adapter of some embodiments is secured by threading on an angular position which mates with threading on the inner surface of the housing. In alternative embodiments, the syringe adapter is not removable or comprises part of the housing.

The triggering mechanism is explained next.

Attention is now turned to FIG. 3A, which, in isometric partial section view, illustrates injector head 10A with the trigger mechanism.

Head 10A comprises housing body 21 with inner surface 21A, which guides spring 23 which guides piston 22 having neck 22A with beveled trigger catch shoulder 24A, trigger latch 25 pivoting on pin 25A and catching at contact 24C, push button 26 with front sliding guide 26A and rear sliding guide 26B and restrainer protrusion 26C and lever contact 26D, button position restoring clip spring 27 with end fixture 27A and sliding tip 27B, housing top retainer 28 with lower stop socket 28A and upper pop-in socket 28B and venting slot 28C, and safety cap 29 with pivot hinge 29A and snap-in recess lock 29B.

The piston is retained within the housing and is movable along the injection axis between a loaded position (as shown) proximal the trigger end and an unloaded position (as will be shown next) proximal the dispensing end.

The piston comprises a piston head proximal to the dispensing end. The syringe adapter is configured to retain the piston in the housing. For example, the piston head in some embodiments is larger than the opening in the syringe adapter (e.g. formed by the annular portion of the syringe adapter.

The piston head in some embodiments includes a portion sized to extend into the opening of the syringe adapter when the piston is in the unloaded position for contacting the plunger of a needle free syringe.

The compression spring is retained within the housing and around the piston. The compression spring is retained around the piston and is further retained by the piston head proximal to the dispensing end. The interior surface of the housing in some embodiments comprises a portion extending towards the injection axis shown in FIG. 1 which blocks the compression spring from contacting the trigger. The piston and compression spring are sized relative to the housing such that the compression spring is compressible along injection axis X within the housing. For example, the outer surfaces of the spring and the piston head in some embodiments slide along the inner surface of the housing.

The configuration of the compression spring in some embodiments is capable of being varied to modify the force in which the piston head will depress the plunger of the needle-free syringe. As a result, it is possible to target different injection depths by choosing different configurations. For example, for subcutaneous injection, the compression spring is capable of being varied depending on the desired depth of penetration. Typical non-limiting examples of spring forces for subcutaneous injection range between 185-10 N to 165-8 N, depending on the degree of fat under the skin. Typical non-limiting examples of spring forces for intramuscular injection are around 200-20 N. Typical non-limiting spring forces for intradermal injection range between 60-5 N and 90-5 N, depending on the age of the subject. The compression spring of various embodiments is capable of thus being configured to provide a spring force of 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245 or 250 N, or greater.

The choice of materials, gauge and coil number to produce a suitable spring to generate these forces is well within the common general knowledge of a person of skill in the art. In one non-limiting example of a spring, the spring material is high carbon spring wire with a wire diameter of 0.4 mm, a mean coil diameter of 3.2 mm, 9 active coils and 11 total coils, a spring stiffness of 0.86 N/mm, and free, working and assembly lengths 25 mm, 19.4 mm and 12.4 mm, respectively. These metrics are merely exemplary, however.

Where the syringe adapter is removable, the housing of some embodiments is capable of being configured to removably accept one or more of alternatively configured syringe adapters, pistons and springs.

The piston is retained in the loaded position by the trigger, which is mounted within the housing proximal to the trigger end and which is movable between a non-actuated position (shown) and an actuated position (not shown) by depression of the push-button. The trigger of some embodiments comprises a lever biased towards the push-button by a return spring disposed within the housing. The return spring in some embodiments is a clip spring, e.g. mounted to the interior surface of the housing or elsewhere in the housing.

The piston further comprises a trigger catch, disposed proximal the trigger end of the housing, i.e. opposite the piston head. The trigger further comprises a trigger latch configured to engage the trigger catch when the trigger is in the non-actuated position and the piston is in the loaded position and to release the trigger catch when the trigger is in the actuated position (not shown). In some embodiments, the trigger catch of the piston comprises an annular engagement surface extending outward from the injection axis X and facing towards the dispensing end of the housing of the fluid injection device. The annular engagement surface in some embodiments extends radially outward from the injection axis. The trigger latch in some embodiments comprises an engagement surface extending inwardly towards the injection axis and facing towards the trigger end of the housing. In such embodiments, the engagement surface of the trigger latch engages the annular engagement surface of the trigger catch when the trigger is in the non-actuated position and clears the trigger catch while the trigger is in the actuated position (not shown).

To facilitate loading of the fluid injection device, the trigger catch of some embodiments is capable of being configured to urge the trigger latch in a direction transverse to the injection axis X when the piston moves from the unloaded position to the loaded position. In some embodiments, the annular engagement surface of the trigger catch comprises an annular beveled surface which faces away from the injection axis towards the trigger end of the housing and the engagement surface of the trigger latch of some embodiments further comprises a beveled surface which faces towards the injection axis and towards the dispensing end of the housing. A loader device further facilitates loading. That is explained further on and illustrated by FIGS. 4A-4C.

Attention is now turned to FIG. 3B, which, in isometric partial section view, illustrates injector 10B, which is injector 10 in unloaded position. Likewise components labeled likewise. Syringe adapter 30 is shown here in section view with housing tread 31B and syringe socket shoulder 31A. The loader is explained next.

Attention is now turned to FIG. 4A, which, in isometric view, illustrates loader assembly 50A with injector 10B positioned to be loaded and lever assembly 60 with loader mechanism 70.

The loader of some embodiments takes the form of a hinged case comprised of top and bottom halves. The loader is movable between an open (as shown) and closed state (not shown). Further details are disclosed in FIGS. 4B and 4C.

Attention is now turned to FIG. 4B, which, in isometric view, illustrates loader compact assembly 50B without injector, readied to load.

Lever assembly 60 comprises lower arm 61, upper arm 62, and arms connector hinge 63. The lower arm has injector receiving socket 61A and sliding guides 61B formed from its body. The upper arm has sliding guide 62As formed between stiffener ribs. Parts of mechanism 70 slide on said guides.

Attention is finally turned to FIG. 4c, which, in isometric view, illustrates loader disassembled assembly 50C without injector, stripped apart for clarity. Likewise components labeled likewise.

Loading mechanism 70 comprises caddy 71 which is abutted by reaction wall 61C, framed plunger 72 with push pin 72A, forcing arm 73 with hinge 73A and slider tips 73B.

To reduce or eliminate force on the external actuation surface of the fluid injection device during loading, the loader of some embodiments is capable of being configured to retain the syringe adapter and prevent movement of the fluid injection device during loading. For example, the syringe adapter of some embodiments comprises an outer surface that extends away from the injection axis beyond the outer surface of the housing. The loader of some embodiments is capable of being configured to receive the fluid injector device on an interior retaining surface comprising a lip adapted to engage the outer surface of the syringe adapter of the fluid injector device. Since the lip of the interior retaining surface of the loader is adapted to engage the extended outer surface of the syringe adapter of the fluid injector device, none of the push-button, safety cap and external actuation surface are stressed against the interior surface of the loader during loading.

Finally, a kit is also disclosed (not shown). The kit comprises a fluid injector device and a loader. The syringe adapter of the fluid injector device of some embodiments is capable of being removable. In some of these embodiments, the kit includes one or more additional compression springs, each of which is distinctly configured to provide a different spring force. Where the syringe adapter is removable, the kit of some embodiments includes one or more additional syringe adapters, each of which is distinctly configured to retain different needle-free syringes, preferably labeled for 0.1-0.5 ml intervals for fluid delivery.

To the skilled in the art of needle free injecting, it shall be obvious that the disclosed and proposed novel features of the invention, including the trigger mechanism, its safety cap, the spring force graduation, the spring loader and the spring-piston kit, all facilitate safer use, simpler mechanism, lesser cost and more ease and speed of use, thus represent great improvement on the state of art.

The present invention is described above with reference to a preferred embodiment. However, those skilled in the art will recognize that changes and modifications may be made in the described embodiment without departing from the nature and scope of the present invention.

For instance, replacing the coil spring with crest-to-crest wave spring is intuitive and thus instructive as being within the scope of the invention. Crest-to-crest springs, known as Smalley Wave Springs, fit smaller space than coil springs for being half as short for the same force, and allow for the proposed force graduation by wave clipping, which greatly reduces manufacturing cost. Wave springs use flat, not round but rolled from round, wires and, in essence, are a series of leaf springs in contact and continuation around a circular path, fitting into a cylindrical space. Wave springs can be laminated to give damping which reduces recoil felt on the push button of the device.

Furthermore, it is also considered within the scope storing one or more springs, pistons or spring-piston sets in the loader in sockets or compartments to be handy for the one who needs only a few different spring force settings. That is, it is considered intuitive and hereby instructive to combine the kit with the loader.

Also considered within the scope accessories facilitating the syringe fill-up from a vial and collar sets enlarging the syringe tip area to be pushed against the skin. In some embodiments, a syringe fill-up accessory includes a vial adapter that creates an appropriate transition/connection between the injection nozzle of the syringe and the opening of a vial from which the syringe is to be filled. In some such embodiments, the vial adapter includes three components, a main body, a lid and an insert. In such embodiments the lid covers a syringe fill side of the main body to protect from contaminants. The lid is removable for filling, to expose a retention mechanism on the main body that positively engages with the injection nozzle of the syringe to hold the syringe in proper position during filling. The main body includes a straw that protrudes from the vial-side of the main body, which opposes the syringe fill side of the main body. The straw extends into the vial for filling the syringe. The main body includes an O-ring seal at the top of the straw for engagement with the syringe nozzle. The vial-side of the main body is sized and shaped to engage with the opening of a large vial, as well as with a first end of the vial adapter. The opposing second end of the vial adapter is sized and shaped to engage with the opening of a smaller vial. In operation, the insert is removed from the main body to connect the vial adapter to a large vial. The insert is left connected to the vial adapter to connect the vial adapter to a small vial.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Although the foregoing detailed description of the present invention has been described by reference to an exemplary embodiment, and the best mode contemplated for carrying out the present invention has been shown and described, it will be understood that certain changes, modification or variations may be made in embodying the above invention, and in the construction thereof, other than those specifically set forth herein, may be achieved by those skilled in the art without departing from the spirit and scope of the invention, and that such changes, modification or variations are to be considered as being within the overall scope of the present invention. Therefore, it is contemplated to cover the present invention and any and all changes, modifications, variations, or equivalents that fall with in the true spirit and scope of the underlying principles disclosed and claimed herein. Consequently, the scope of the present invention is intended to be limited only by the attached claims, all matter contained in the above description and shown in the accompanying drawings shall be interpreted as illustrative and not in a limiting sense.

Having now described the features, discoveries and principles of the invention, the manner in which the invention is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. A fluid injection device, comprising:
a housing comprising an inner surface and an outer surface which extend from a proximal trigger end to a distal dispensing end along an injection axis;
a housing top retainer at said trigger end comprising a lower stop socket, an upper pop-in socket, a venting slot, an external actuation surface disposed transverse to the injection axis at the trigger end, the external actuation surface comprising a surface that tapers downward towards the dispensing end, and a safety cap, said safety cap comprising a pivot hinge and a snap-in recess lock;
wherein said venting slot is positioned at a distal portion of said housing top retainer near said lower stop socket;
a syringe adapter at the dispensing end of the housing, the syringe adapter configured to retain a needle-free syringe such that a plunger of the needle-free syringe is movable within the housing along the injection axis;
wherein said syringe adapter comprises an outer surface that extends away from the injection axis beyond the outer surface of the housing;
a piston retained within the housing by the syringe adapter and movable along the injection axis between a loaded position near the trigger end and an unloaded position near the dispensing end, the piston comprising a piston head near the dispensing end and a trigger catch near the trigger end of the housing, the piston head being movably positioned to bias the plunger of the needle-free syringe along the injection axis;
a compression spring associated with the piston, the piston and compression spring sized relative to the housing such that the compression spring is compressible along the injection axis within the housing;
a trigger mounted within the housing near the trigger end and movable between a non-actuated position and an actuated position by depression of a push-button disposed at the external actuation surface of the housing, the trigger comprising a trigger latch configured to engage the trigger catch when the trigger is in the non-actuated position and the piston is in the loaded position and to release the trigger catch when the trigger is in the actuated position, wherein the trigger catch is configured to urge the trigger latch in a direction transverse to the injection axis when the piston moves from the unloaded position to the loaded position; and wherein the housing, syringe adapter, and needle-free syringe are configured such that a gas within and a sound created within the housing are directed out the venting slot upon actuation of said fluid injection device.

2. The fluid injection device of claim 1, wherein:
the trigger catch comprises an annular engagement surface extending radially outward from the injection axis and facing towards the dispensing end of the housing; and the trigger latch comprises an engagement surface extending inwardly towards the injection axis and facing towards the trigger end of the housing, and which engages the annular engagement surface of the trigger catch when the trigger is in the non-actuated position and clears the trigger catch when the trigger is in the actuated position.

3. The fluid injection device of claim 1, wherein:
the trigger catch further comprises an annular beveled surface which faces away from the injection axis towards the trigger end of the housing; and the trigger latch further comprises a beveled surface which faces towards the injection axis and towards the dispensing end of the housing.

4. The fluid injection device of claim 1, wherein the trigger further comprises a lever biased towards the push-button by a return spring disposed within the housing.

5. The fluid injection device of claim 4, wherein the return spring is a clip spring biased against the lever of the trigger.

6. The fluid injection device of claim 1, wherein the safety cap is pivotally mounted to the external actuation surface of the housing top retainer.

7. The fluid injection device of claim 1, wherein the interior surface of the housing comprises a portion extending towards the injection axis and which blocks the compression spring from contacting the trigger.

8. The fluid injection device of claim 1, wherein the syringe adapter is removable, and the housing is configured to removably accept alternatively configured syringe adaptors.

9. The fluid injection device of claim 8, wherein:
the syringe adapter is removable;
the syringe adapter is connected to the injector via turning clockwise;
the piston and the compression spring are removable from the housing when the syringe adapter is removed from the housing; and
the housing is configured to removably accept at least one of the alternatively sized pistons and springs.

10. The fluid injection device of claim 1, wherein the syringe adapter is removably affixed to the dispensing end of the housing.

11. The fluid injection device of claim 1, wherein the syringe adapter is irremovably affixed to the dispensing end of the housing.

12. The fluid injection device of claim 1, wherein the compression spring is retained around the piston by the piston head.

13. The fluid injection device of claim 1, wherein:
the housing inner surface comprising a narrowed inner surface section narrower than the compression spring but wider than the piston;
said narrowed inner surface forms a shelf for compressing said compression spring;
said piston comprises a tapered neck near a proximal end of the piston distal of the trigger catch; and
said tapered neck extends into said narrowed inner surface with said piston in loaded position.

14. The fluid injection device of claim 1, further comprising:
a loader comprising an interior retaining surface configured to receive the housing and the syringe adapter;
wherein the loader is movable about a hinge between an open state and a closed state;
wherein movement of the loader from said open state to said closed state is configured to extend a loader plunger through an open end of the syringe adapter to make contact with said piston head within the housing and to counteract the compression spring to push the piston from said unloaded position into said loaded position;
wherein said interior retaining surface comprises a lip configured to engage the syringe adapter outer surface; and
wherein engagement of the syringe adapter outer surface with said lip is configured to retain the syringe adapter and the housing within said interior retaining surface without stress on the housing trigger end when the piston is pushed from said unloaded position into said loaded position.

15. A fluid injection device, comprising:
a housing comprising an inner surface and an outer surface which extend from a proximal trigger end to a distal dispensing end along an injection axis;
a needle-free syringe comprising a plunger, a dispenser capsule, a threaded head, a head stop shoulder, and an injection nozzle, said plunger being moveable within the housing;
a piston retained within the housing and movable between a loaded position and an unloaded position to bias the plunger of the needle-free syringe;
a syringe adapter at the dispensing end of the housing, the syringe adapter configured to retain the needle-free syringe and thereby create a seal of the dispensing end and wherein the needle-free syringe is removable;
said syringe adapter comprising an outer surface that extends away from the injection axis beyond the outer surface of the housing;
a trigger mounted near the trigger end and movable between a non-actuated position and an actuated position to initiate movement of the piston from the loaded position to the unloaded position upon actuation of the trigger;
a housing top retainer at said trigger end comprising an external actuation surface disposed transverse to the injection axis at the trigger end, the external actuation surface comprising a surface that tapers downward towards the dispensing end;
said housing top retainer further defining a venting slot positioned at a distal portion of said housing top retainer; and
wherein the housing, syringe adapter, and needle-free syringe are configured such that a gas within and a sound created within the housing are directed out the venting slot upon actuation of said fluid injection device.

16. The fluid injection device of claim 15, wherein a thickness between the inner surface and the outer surface reduces an amount of sound from passing through the housing surfaces.

17. The fluid injection device of claim 16, wherein said housing is a metal material.

18. The fluid injection device of claim 17, wherein said material is stainless steel.

19. The fluid injection device of claim 15, wherein the sound created within the housing only exits the housing through the trigger end opening.

20. The fluid injection device of claim 15, further comprising:
- a loader comprising an interior retaining surface configured to receive the housing and the syringe adapter;
- wherein the loader is movable about a hinge between an open state and a closed state;
- wherein movement of the loader from said open state to said closed state is configured to extend a loader plunger through an open end of the syringe adapter to make contact with said piston within the housing and to push the piston from said unloaded position into said loaded position;
- wherein said interior retaining surface comprises a lip configured to engage the syringe adapter outer surface; and
- wherein engagement of the syringe adapter outer surface with said lip is configured to retain the syringe adapter and the housing within said interior retaining surface without stress on the housing trigger end when the piston is pushed from said unloaded position into said loaded position.

21. A fluid injection device, comprising:
- a housing comprising an inner surface and an outer surface which extend from a proximal trigger end to a distal dispensing end along an injection axis;
- a housing top retainer at said trigger end comprising a venting slot and an external actuation surface disposed transverse to the injection axis at the trigger end, the external actuation surface comprising a surface that tapers downward towards the dispensing end;
- wherein said venting slot is positioned at a distal portion of said housing top retainer;
- a syringe adapter at the dispensing end of the housing, the syringe adapter configured to retain a needle-free syringe and thereby create a seal of the dispensing end;
- said syringe adapter comprising an outer surface that extends away from the injection axis beyond the outer surface of the housing;
- a piston retained within the housing and movable between a loaded position and an unloaded position to bias the plunger of the needle-free syringe;
- a trigger mounted near the trigger end on the injection axis and movable between a non-actuated position and an actuated position to initiate movement of the piston from the loaded position to the unloaded position upon actuation of the trigger, said trigger comprising a push button with a front sliding guide, a rear sliding guide, a restrainer protrusion, and a lever contact;
- a loader comprising an interior retaining surface configured to receive the housing and the syringe adapter;
- wherein the loader is movable about a hinge between an open state and a closed state;
- wherein movement of the loader from said open state to said closed state is configured to extend a loader plunger through an open end of the syringe adapter to make contact with said piston within the housing and to push the piston from said unloaded position into said loaded position;
- wherein said interior retaining surface comprises a lip configured to engage the syringe adapter outer surface;
- wherein engagement of the syringe adapter outer surface with said lip is configured to retain the syringe adapter and the housing within said interior retaining surface without stress on the housing trigger end when the piston is pushed from said unloaded position into said loaded position; and
- wherein the housing, syringe adapter, and needle-free syringe are configured such that a gas within and a sound created within the housing are directed out the venting slot upon actuation of said fluid injection device.

22. The fluid injection device of claim 21, wherein the trigger is actuated by depression of the push-button disposed at the external actuation surface of the housing.

23. The fluid injection device of claim 22, wherein the trigger comprises a trigger latch configured to engage a trigger catch when the trigger is in the non-actuated position and the piston is in the loaded position and to release the trigger catch when the trigger is in the actuated position, wherein the trigger catch is configured to urge the trigger latch in a direction transverse to the injection axis when the piston moves from the unloaded position to the loaded position.

\* \* \* \* \*